US010596261B2

(12) United States Patent
Tewari et al.

(10) Patent No.: US 10,596,261 B2
(45) Date of Patent: *Mar. 24, 2020

(54) COPROCESSED SILICA COATED POLYMER COMPOSITION (71) Applicant: HERCULES INCORPORATED, Wilmington, DE (US)

(72) Inventors: Divya Tewari, West Chester, PA (US); Yevgeniya A. Titova, Wilmington, DE (US); Brad Beissner, Wilmington, DE (US); Thomas Durig, Chadds Ford, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/764,921

(22) PCT Filed: Mar. 12, 2014

(86) PCT No.: PCT/US2014/024956
§ 371 (c)(1),
(2) Date: Jul. 30, 2015

(87) PCT Pub. No.: WO2014/165246
PCT Pub. Date: Oct. 9, 2014

(65) Prior Publication Data
US 2015/0359895 A1 Dec. 17, 2015

Related U.S. Application Data (60) Provisional application No. 61/777,604, filed on Mar. 12, 2013.

(51) Int. Cl.
A61K 47/32 (2006.01)
A61K 47/02 (2006.01)
(Continued)

(52) U.S. Cl.
CPC ............ *A61K 47/32* (2013.01); *A61J 3/10* (2013.01); *A61K 9/2009* (2013.01);
(Continued)

(58) Field of Classification Search
None
See application file for complete search history.

(56) References Cited

U.S. PATENT DOCUMENTS

2001/0001664 A1    5/2001  Sherwood et al.
2004/0186184 A1*   9/2004  Berlin .................. A61K 31/135
                                                              514/649
(Continued)

FOREIGN PATENT DOCUMENTS

WO    WO2011133956 A1    10/2011

OTHER PUBLICATIONS

International Search Report, PCT/US2014/024956 published on Oct. 9, 2014.

*Primary Examiner* — Bethany P Barham
*Assistant Examiner* — Barbara S Frazier
(74) *Attorney, Agent, or Firm* — William J. Davis; Nathalie Tietcheu (57) ABSTRACT The present invention provides a coprocessed excipient composition and a method of producing the same. The coprocessed excipient comprises vinyl lactam derived polymer and a deagglomerated coprocessing agent. The coprocessing agent is fumed silica, colloidal silica or silicon dioxide. The coprocessed excipient is prepared by a continuous process and has a Brookfield cohesion of less than 0.12 kPa, a bulk density of at least 0.249 gram/milliliter and a flow property as measured by Johanson flow rate number increase from 1.1 to 5.0 fold.

13 Claims, 3 Drawing Sheets

1) Milling Feed
2) Rotor
3) Impact Beater
4) Milling Gap
5) Stator
6) Outlet Gap
7) Alternative Stator (Screen) with Outlet Through the Screen Perforation (51) Int. Cl.
*A61K 47/38* (2006.01)
*A61K 9/20* (2006.01)
*A61K 31/522* (2006.01)
*A61J 3/10* (2006.01)
*C09D 139/06* (2006.01)
*C09J 139/06* (2006.01)

(52) U.S. Cl.
CPC .......... *A61K 9/2027* (2013.01); *A61K 9/2054* (2013.01); *A61K 31/522* (2013.01); *A61K 47/02* (2013.01); *A61K 47/38* (2013.01); *C09D 139/06* (2013.01); *C09J 139/06* (2013.01)

(56) References Cited

U.S. PATENT DOCUMENTS

| | | | |
|---|---|---|---|
| 2010/0209498 A1* | 8/2010 | Jain | A61K 9/4808 424/456 |
| 2010/0285164 A1* | 11/2010 | Schaible | A61K 9/0056 424/777 |
| 2010/0288665 A1* | 11/2010 | Lomaga | A61K 31/137 206/438 |
| 2012/0178822 A1 | 7/2012 | Rao et al. | |

* cited by examiner

FIG. 1

1) Milling Feed
2) Rotor
3) Impact Beater
4) Milling Gap
5) Stator
6) Outlet Gap
7) Alternative Stator (Screen) with Outlet Through the Screen Perforation

FIG. 2

Gravitational force
Promotes flow
increases with higher density

Inter-particle cohesion counteracts flow
Increases with smaller particle size, surface roughness, particle irregularity, moisture and charge

FIG. 3

COPROCESSED SILICA COATED POLYMER COMPOSITION

FIELD OF THE INVENTION

The present invention relates to a coprocessed excipient composition and to a method of producing the same. The present invention particularly relates to a coprocessed excipient comprising vinyl lactam derived polymer and a deagglomerated coprocessing agent.

BACKGROUND OF THE INVENTION

Excipient powders frequently exhibit poor flow and compaction behavior. Various techniques such as wet granulation, spray drying, mechanofusion, and grinding have been employed to improve the flow and compaction behavior.

U.S. Pat. No. 4,734,285 assigned to Dow Chemical Company discloses delayed release solid tablets of a therapeutically active composition and a process to prepare such a composition. Fine particles, which can pass through a 100 mesh screen (149 micrometer mesh size) and preferably 140 mesh screen (105 micrometer mesh size), of hydroxypropyl methylcellulose ether are present as an excipient in the tablet composition. These fine particles are very small in size and shows poor flow properties. Poor particle flow can lead to consolidation of the powder bed in processing equipment, such as storage bins and tablet press feed hoppers. Problems can include increased inconsistency in tablet weight or tablet crushing strength from tablet-to-tablet as well as inconsistency in the amount of active ingredient incorporated into each dosage form.

WO2004/022601 assigned to JRS Pharma LP and U.S. Pat. No. 5,585,115 assigned to Edward H. Mendell Co., Inc. disclose an agglomerated microcrystalline cellulose blend containing silicon dioxide, purported to have improved compressibility. The disclosure states that silicon dioxide is a critical component to improve compressibility. The two step process described includes spray granulation followed by wet granulation. The prepared granules in this process are further dried using heat, which is not advantageous. However, granulation is a time consuming and adds cost to the process, due to the time lost, additional labor, energy consumption and additional equipment required.

Several processes for drying-grinding moist cellulose derivatives are known in the art, such as described in the patent applications GB 2262527A; EP 0 824 107 A2; EP-B 0 370 447 (equivalent to U.S. Pat. No. 4,979,681); EP 1 127 895 A1 (equivalent to U.S. Pat. No. 6,509,461); EP 0 954 536 A1 (equivalent to U.S. Pat. No. 6,320,043); WO96/00748 A1; WO2011/046679 (equivalent to US 2012/187225) and WO2012/138532.

US2012/160944A1 assigned to ICEUTICA PTY LTD discloses a method to produce nano and micro-particle powders of a biologically active material which have improved powder handling properties using dry milling process.

WO2012/116402A1 assigned to University of Monash discloses binder powders for use in powder material processing and processes for their preparation by using techniques such as spray drying and mechanofusion. These processes lead to reduction in particle size of the polymer. Moreover, these processes are costly and time consuming US2012/0178822A assigned to ISP INVESTMENTS INC discloses coprocessing of PVP and calcium silicate by using ball milling, spray drying or freeze drying.

The increase in flow of cellulose polymers by co-milling microcrystalline cellulose with nano-silica is described in J. Pharm. Sci. 2011 November; 100(11):4943-52, Chattoraj S, Shi L, Sun CC.

Moreover, spray drying, mechanofusion, magnetic assisted impaction, hybridizer, and grinding require specialized instruments that are commonly not available at manufacturing units.

Surprisingly, it has been found that bulk density and flowability of vinyl lactam derived polymers can be increased by a novel continuous process comprising coprocessing the polymer and a coprocessing agent using high shear.

Thus, the present invention relates to a coprocessed excipient composition comprising vinyl lactam derived polymer and a deagglomerated coprocessing agent. The coprocessed excipient is prepared in a continuous process and has excellent compactability and improved flow property as measured by Johanson flow rate number increase from 1.1 to 5.0 fold, is characterized by a Brookfield cohesion of less than 0.12 kPa and a bulk density of at least 0.249 g/ml. The coprocessing agent is fumed silica, colloidal silica, silicon dioxide, calcium silicate or a combination thereof.

SUMMARY OF THE INVENTION

The present invention provides a coprocessed excipient comprising vinyl lactam derived polymer or a blend and a deagglomerated coprocessing agent. The coprocessed excipient is prepared in a continuous process and has a Brookfield cohesion of less than 0.12 kPa and a bulk density of at least 0.249 gram/milliliter and a flow property as measured by Johanson flow rate number increase from 1.1 to 5.0 fold.

The vinyl lactam derived polymer used in the present invention can be selected from the group comprising N-vinyl-2-pyrrolidone, poly(vinyl pyrrolidone), polyvinyl poly pyrrolidone, N-vinyl-2-caprolactam, N-vinyl-3-methyl-2-pyrrolidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, and/or combinations thereof.

In a particular embodiment the coprocessing agent is selected from fumed silica, colloidal silica, silicon dioxide, calcium silicate or a combination thereof.

The lactam derived polymer is present in an amount of about 90.0% to about 99.9%. The coprocessing agent is present in an amount of about 0.1% w/w to about 10.0% w/w of the total coprocessed excipient composition.

In one of the particular embodiment, the weight ratio of the lactam derived polymer to coprocessing agent is about 90:10, 95:5, 98:2, 99:1 or even 99.9 to 0.1.

The coprocessed excipient of the present invention is further combined with an active or functional ingredient selected from paints and coatings, personal care, detergents, pharmaceuticals, neutraceuticals, ceramics, insulators, pet food, animal food and human food, agricultural products, adhesives, electroplating, inks, dyes, paper, catalytic convertors and electronics.

Yet another aspect of the present invention provides a process to prepare coprocessed excipient comprising the steps of:

i. deagglomerating coprocessing agent using shear in magnitude of at least 0.01kW-hr/kg;
ii. passing the lactam derived polymer blend thereof and deagglomerated coprocessing agent through a blender with an average particle residence time of >1 second;
iii. subjecting the above two components to pass through a universal mill;
iv. maintaining an average particle residence time within the universal mill system to be >1 seconds completed by a continuous recycle process; and
v. obtaining the coprocessed excipient having a Brookfield cohesion of less than 0.12 kPa, a bulk density of at least 0.249 gram/milliliter and a flow property as measured by Johanson flow rate number increased from 1.1 to 5.0 fold.

In a preferred embodiment, the universal mill consists of a rotor with tip speed for about 15 meters/second to about 150 meters/second and screen size of about 0.2 millimeter to about 0.9 millimeter.

The composition can be used in various industrial applications including paints and coatings, personal care, detergents, pharmaceuticals, neutraceuticals, ceramics, insulators, pet food, animal food and human food, agricultural products, adhesives, electroplating, inks, dyes, paper, catalytic convertors and electronics.

In a preferred embodiment, the composition is used in pharmaceuticals.

In a preferred embodiment, the composition is formulated into an oral dosage form, such as a tablet, by dry granulation, direct compression or hot melt extrusion processing.

The present invention provides a directly compressible pharmaceutical composition comprising an active pharmaceutical ingredient and coprocessed excipient.

Yet another aspect of the present invention provides a direct compression process comprising the steps of i) blending an active pharmaceutical ingredient, the above-described coprocessed excipient, and optionally one or more pharmaceutically acceptable adjuvants to produce a blend with improved flow property and
ii) compressing the resulting composition to get a product with improved drug content uniformity and improved compactability.

In a preferred embodiment, the directly compressible pharmaceutical composition is formulated into modified release, controlled release, sustained release, immediate release, extended release dosage forms.

The present invention provides a process to prepare a directly compressible pharmaceutical composition comprising blending the active pharmaceutical ingredient, the coprocessed excipient having a Brookfield cohesion of less than 0.12 kPa, a bulk density of at least 0.249 gram/milliliter and a flow property as measured by Johanson flow rate number increased from 1.1 to 5.0 fold, and optionally one or more adjuvants and compressing the resulting components to obtain directly compressible pharmaceutical composition.

DETAILED DESCRIPTION OF THE INVENTION

Figure 1:
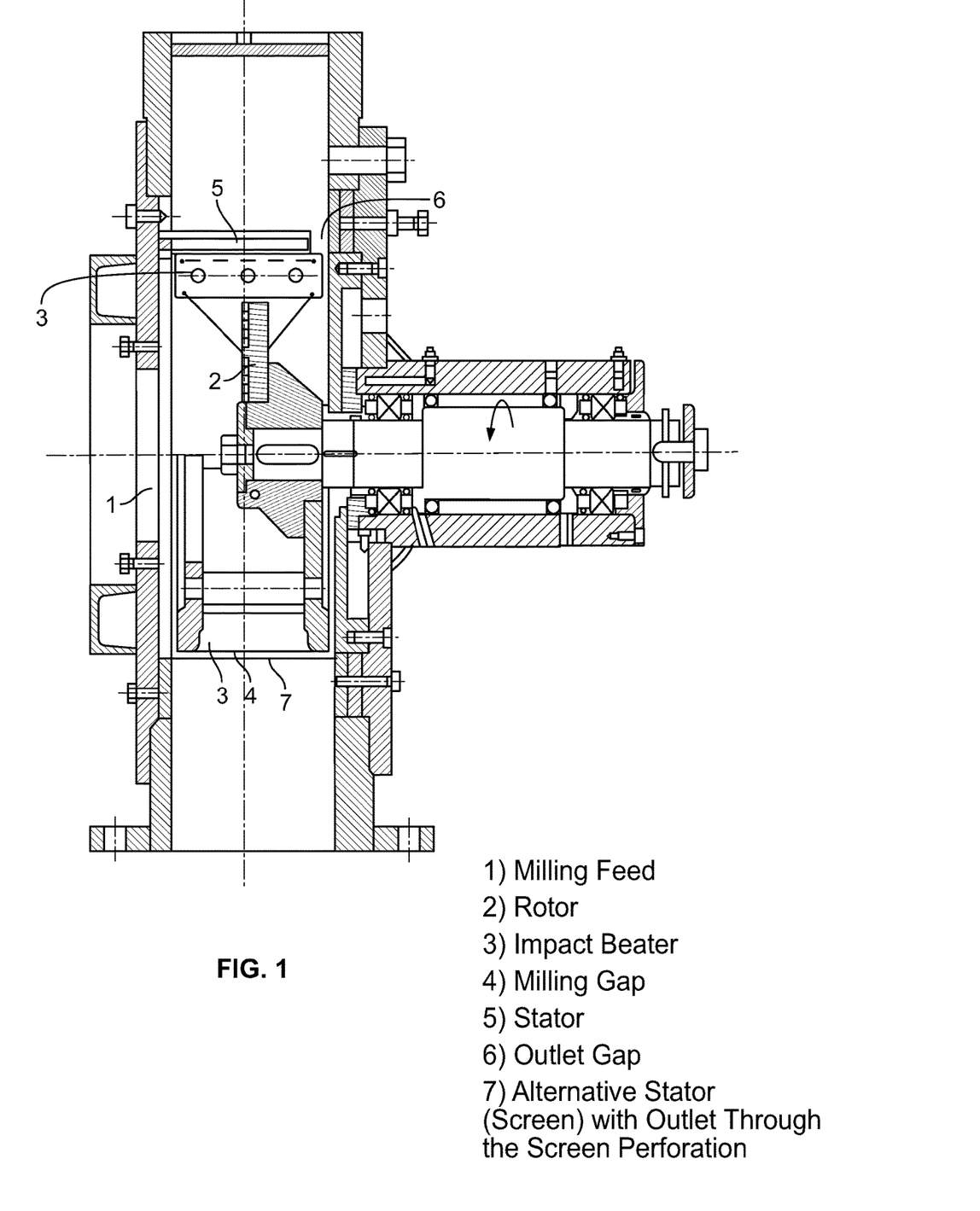
FIG. 1 represents a diagram of a universal mill and its various parts
Figure 2:
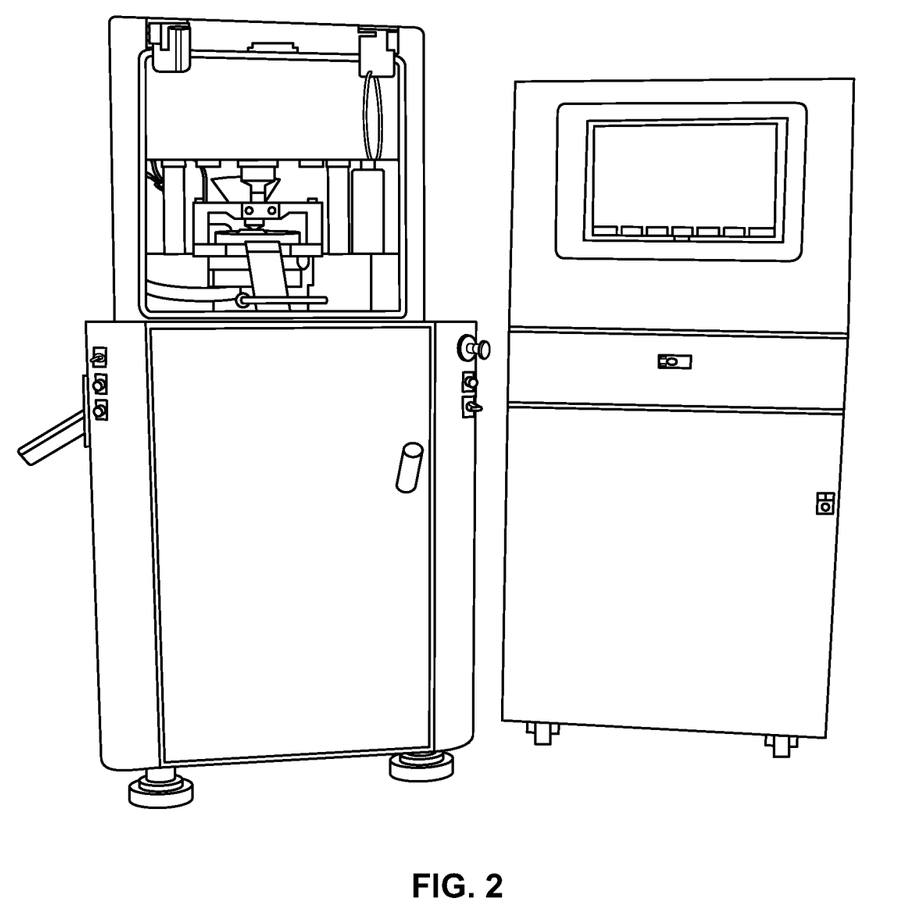
FIG. 2 represents a diagram of a STYLCAM 200R, a single-punch rotary tablet press
Figure 3:
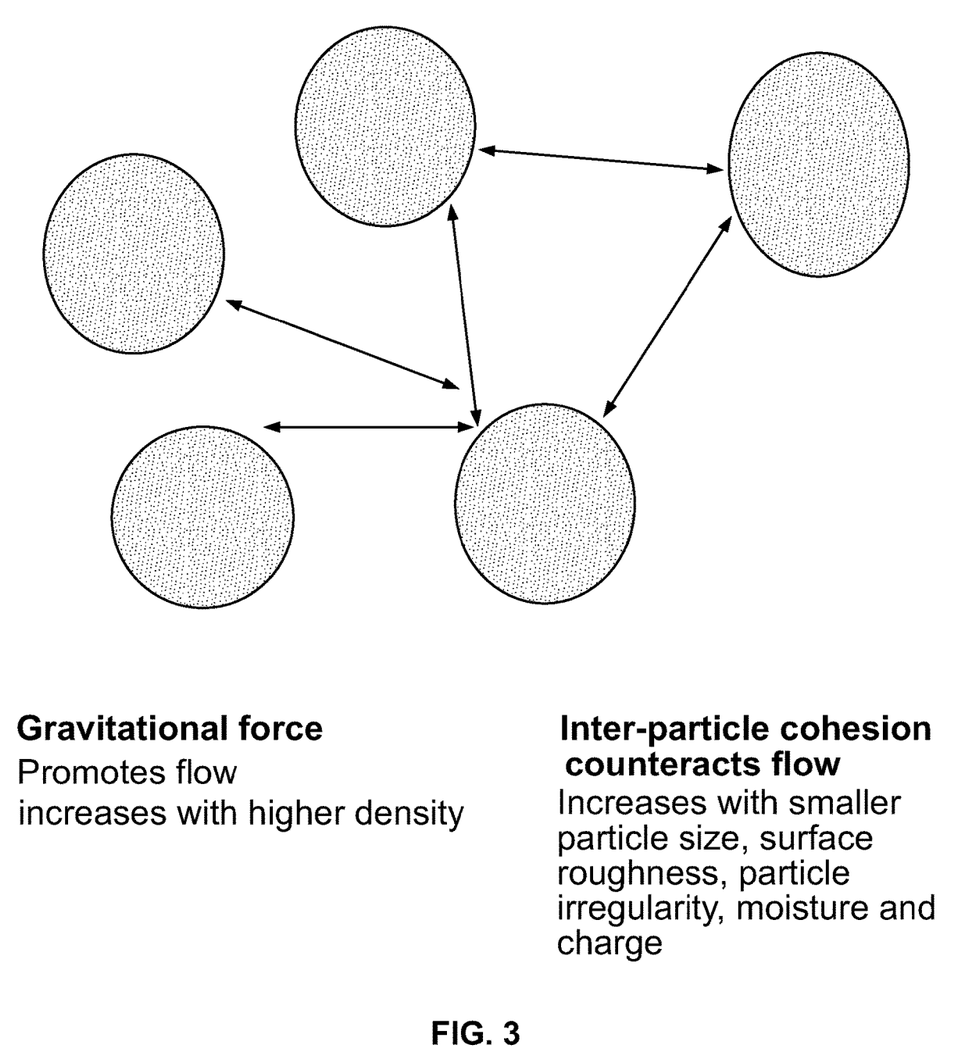
FIG. 3 represents enhanced flow as a result of low Interparticle Brookfield Cohesion

Typical polymers used for the direct compression formulations have a fibrous nature, small particle size, strong inter-particle cohesion and surface charge, which lead to a poor flow in pharmaceutical unit process. Formulators often have to use a granulation step to overcome these challenges to powder flow. The powder flow is affected by gravitational forces (influenced by bulk density) and the interparticle cohesion and a balance is needed between the two to improve the flow (as shown in FIG. 7). Not to be bound by any theories, the inventors of the present invention discovered the increased flowability is observed when an additive is coprocessed with the polymeric powder whose flowability is to be increased. Enhanced flow rate of almost 5 fold was achieved as a result of very low interparticle cohesion and higher bulk density.

There are several advantages for using the coprocessed excipient of the present invention: (i) reduced processing time and production costs, no additional capital investment is necessary for adopting this flow-improvement technique; (ii) improved powder flow; (iii) improved content uniformity (iv) dissolution profiles comparable with other commercial polymeric grade available in the market; (v) the present process is fast, continuous, and scalable. Hence, it can be readily adopted during both development and manufacturing of pharmaceutical products.

Throughout this specification and the claims which follow, unless the context requires otherwise, the word "comprise" and variations such as "comprises" and "comprising", will be understood to imply the inclusion of a stated integer or step or group or integers or steps but not the exclusion of any other integer or step or group or integers or steps.

The singular forms "a", "an" and "the" include plural aspects unless the context clearly dictates otherwise.

All aspects, embodiments and examples described herein are encompassed by the term "invention".

As used herein, the term "m/sec" refers to the units of rotor speed in meters per second.

As used herein, the term "mm" refers to the units of mesh size in millimeters.

As used herein, the term "bulk density" refers to Bulk density (BD) is defined as the ratio of apparent volume to mass of the material taken, called untapped bulk density, and also the ratio of tapped volume to mass of material taken, called tapped bulk density. A useful procedure for measuring these bulk densities is described in United States Pharmacopeia 24, Test 616 "Bulk Density and Tapped Density," United States Pharmacopeia Convention, Inc., Rockville, Md., 1999.

As used herein, the term "Flow Rate Indicizer" refers to an instrument manufactured by Johanson that was used to characterize properties such as FRI (flow rate index), FDI (Flow density index), BDI (Bin density index), and SBI (Spring back index).

As used herein, the term "Johanson flow rate number" refers to Flow Rate Index (FRI), which is a measure of a powder's limiting flow rate through a container after deaeration. The negative direction for the FRI is a decrease. The FRI is also useful for correlating particle sizes and size distribution if the mean particle size remains constant. A lower FRI indicates a smaller particle size or a wider size distribution if the mean size remains unchanged.

As used herein, the term "deagglomeration" refers to a process of breaking up or dispersing that which has agglomerated, aggregated, or clustered together.

The term "coprocessed excipient composition" as used herein, refers to a coprocessed excipient that is a combination of two or more compendial or non-compendial excipients designed to physically modify their properties in a manner not achievable by simple physical mixing and without significant chemical change.

As used herein, the term "Universal Mill" refers to a high speed fine impact mill for the dry grinding or deagglomerating of various products. In particular the mill is utilized as a rotor impact mill, which is characterized by an impact process between the rotor and a stator (such as a screen). Material and air enter the mill and are subject to centrifugal forces from the rotor; subsequently the impact beater forces the material through the milling gap provided by the stator (grinding track and screen). Various configurations of the rotor/impact beater include the wing beater and blast rotor.

As used herein, the term "Blender" refers to a continuous single or double helix ribbon blender with a residence time of at least one second; or a blender with similar capability that allows for mixing in a continuous process, a residence time of at least one second, and shaft speed of 10-30 rotations per minute.

The term "Brookfield Cohesion" as used herein, refers to failure strength measured at an applied compression force in time consolidation test of Brookfield powder flow tester (ASTM D6128). In preferred embodiments, the Brookfield cohesion of the composition of this invention is less than 0.10 kPa and more preferably less than 0.08 kPa.

The term "compaction" as used herein, is a simultaneous process of compression and consolidation of a two phase system (solid-air) due to the applied force.

As used herein, the term "Direct compression" or "DC" refers to obtaining a formulation by directly compressing and molding a raw material powder. This process is described in publications such as The Theory and Practice of Industrial Pharmacy (Third Edition) (Leon Lachman, et al.: LEA & FEBIGER 1986) and Pharmaceutical Dosage Forms: Tablets Volume 1 (Second Edition) (Herbert A. Lieberman, et al.: MARCEL DEKKER INC. 1989).

As used herein, the term "continuous process" refers to production that is not executed batch wise but steadily, such as production on a continuous blend. In non-continuous processes, i.e, batch production processes, insertion of the raw materials into the machine/mill and subsequent unloading of the newly produced composition from the machine/mill occupies too much time to make low-cost production possible. The significance of the term "continuous production" here is the implication of the advantages gained by an assembly line with each step characterized by an average residence time.

The present invention provides a coprocessed excipient comprising a vinyl lactam derived polymer or a blend and a deagglomerated coprocessing agent.

The coprocessed excipient is prepared in a continuous process and has a bulk density of at least 0.249 gram/milliliter and improved flow property as measured by Johanson flow rate number increased from 1.1 to 5.0 fold. The coprocessing agent is fumed silica, colloidal silica, silicon dioxide, calcium silicate or a combination thereof.

Vinyl lactam derived polymers useful in the practice of the present invention can be selected from the group comprising N-vinyl-2-pyrrolidone, poly(vinyl pyrrolidone) (PVP), polyvinyl poly pyrrolidone (PVPP), N-vinyl-2-caprolactam, N-vinyl-3-methyl-2-pyrrolidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, and/or combinations thereof.

The term "Polyvinyl pyrrolidone (PVP)" as used herein, including the claims, refers to a polymer available in different pharmaceutical grades. A particularly preferred source of polyvinyl pyrrolidone is Ashland Specialty Ingredients (Wilmington, Del.), which markets "PVP" under the trade name of Plasdone™ Povidone.

The terms "Polyvinyl polypyrrolidone" or "Crospovidone" as used herein, including the claims, refers to a polymer available in different pharmaceutical grades. A particularly preferred source of crosslinked polyvinyl pyrrolidone is Ashland Specialty Ingredients (Wilmington, Del.), which markets "PVPP" under the trade name of Polyplasdone XL®, Polyplasdone XL-10®, Polyplasdone INF-10, Polyplasdone ultra, and Polyplasdone ultra 10.

Preferably silica useful in the practice of the present invention is selected from the group comprising fumed silica, colloidal silica, silicon dioxide, calcium silicate and/or combinations thereof.

Silica useful in the practice of the present invention is silicon dioxide, particularly colloidal silicon dioxide that has particles size particularly less than 500 nm, more particularly less than 400 nm. Those skilled in the art will appreciate that the name and/or method of preparation of the silicon dioxide utilized in the present invention is not determinative of the usefulness of the product. Rather, it has been surprisingly discovered that it is the physical characteristics of the silicon dioxide which are critical. In particular, it has been discovered that silicon dioxide having a relatively large particle size (and correspondingly small surface area), such as silica gel, is not useful in the current invention Silica itself is a submicron, fluffy, light, loose, bluish-white, odorless and tasteless amorphous powder which is commercially available from a number of sources, including Cabot Corporation (under the tradename Cab-O-Sil); Degussa, Inc. (under the tradename Aerosil®); E.I. DuPont & Co.; and W.R. Grace & Co. Colloidal silicon dioxide is also known as colloidal silica, fumed silica, amorphous fumed silica, silicon dioxide, amorphous silica, light anhydrous silicic acid, silicic anhydride, and silicon dioxide fumed, among others. However, the amount of silicon dioxide included in pharmaceutical applications is limited and it is in the range of 0.01-1% by weight. Handbook of Pharmaceutical Excipients, COPYRGT. 1986 American Pharmaceutical Association, page 255.

In further embodiments, the lactam derived polymer is present in an amount of about 90.0% to about 99.9% and coprocessing agent is present in an amount of about 0.1% w/w to about 10.0% w/w of the total coprocessed excipient composition.

In one particular embodiment, the weight ratio of the lactam derived polymer to coprocessing agent is about 90:10, 95:5, 98:2, 99:1 or even 99.9 to 0.1. Alternatively, the amount coprocessing agent may be expressed as wt/wt %, of the lactam derived polymer, for example, 0.1%, 0.25%, 0.5%, 0.75%, 1.0%, 2.5%, 5%, or 10%.

The present coprocessed excipient can be further combined with an active or functional ingredient selected from paints and coatings, personal care, detergents, pharmaceuticals, neutraceuticals, ceramics, insulators, pet food, animal food and human food, agricultural products, adhesives, electroplating, inks, dyes, paper, catalytic convertors and electronics.

The present invention provides a continuous process to prepare coprocessed excipient comprising the steps of
i. deagglomerating coprocessing agent using shear in magnitude of at least 0.01kW-hr/kg;
ii. passing a lactam derived polymer and deagglomerated coprocessing agent through a blender with an average particle residence time of >1 second;
iii. subjecting the above two components to pass through a universal mill;
iv. maintaining an average particle residence time within the universal mill system to be >1 seconds completed by a continuous recycle process; and
v. obtaining the coprocessed excipient having a Brookfield cohesion of less than 0.12 kPa, a bulk density of at least 0.249 gram/milliliter and a flow property as measured by Johanson flow rate number increased from 1.1 to 5.0 fold.

In further embodiments, the universal mill consists of a rotor with tip speed for about 15 meters/second to about 150 meters/second and screen size of about 0.2 millimeter to about 0.9 millimeter The present invention provides a direct compressible pharmaceutical composition comprising an active pharmaceutical ingredient, which is not more than 1.0% of the coprocessed excipient and optionally one or more pharmaceutically acceptable additives. The direct compression process comprising the steps of
i. blending the active pharmaceutical ingredient, the coprocessed excipient having a Brookfield cohesion of less than 0.12 kPa, a bulk density of at least 0.249 gram/milliliter and a flow property as measured by Johanson flow rate number increase from 1.1 to 5.0 fold, and optionally one or more adjuvants without adding a substantial amount of added solvent or heat; and
ii. compressing the resulting components to obtain directly compressible pharmaceutical composition.

The present invention provides a direct compressible pharmaceutical composition comprising an active pharmaceutical ingredient, the above-described coprocessed excipient and optionally one or more pharmaceutically acceptable additives.

The present invention provides a direct compression process comprising the steps of,
i. blending the active pharmaceutical ingredient, the coprocessed excipient having a Brookfield cohesion of less than 0.12 kPa bulk density of at least 0.249 gram/milliliter and improved flow property as measured by Johanson flow rate from about 1.1 to about 5.0 fold, and optionally one or more adjuvants without adding a substantial amount of added solvent or heat; and
ii. compressing the resulting components to obtain directly compressible pharmaceutical composition.

The following examples further illustrate the invention.

EXAMPLE 1

Coprocessing of Polyvinyl pyrrolidone ("Plasdone" or "PVP") and Deagglomerated Silica (Cab-O-Sil).

The coprocessing performed by co-milling powdered polyvinyl pyrrolidone (Grade: Plasdone) with silica. The silica-coating of the polyvinyl pyrrolidone (Plasdone) was accomplished by geometric dilution of the powdered polymer with silica by sieving and then passing through a blender and then through a universal mill, which is fitted with a blunt impeller. The steps include deagglomeration of silica powder and subsequently at least with a partial coating of silica on the powdered polymer. The speed of the impeller was 3000 rpm and screen size was 0.5 mm and mesh size is 35 with 0.0075 inches during the process.

EXAMPLE 2

Coprocessing of Crosslinked Polyvinyl pyrrolidone ("Crospovidone") and Silica.

The same process described in Example 1 was repeated with crosslinked polyvinyl pyrrolidone ("PVPP") and silica by replacing the mesh size to 50.

EXAMPLE 3

Flow Characterization Measurement of Polymers by Using Johanson Flow Rate Indicizer All components of the test cell and machine pistons were cleaned. Air connections and air pressure were checked and the air pressure was kept at 25 psi. Weight of the empty test cell was measured and recorded. Crosslinked polyvinyl pyrrolidone sample was fluffed up to break-up lumps and to bring material to minimum bulk density. The sample was loaded and it was distributed evenly by using a spoon. The sample was filled just above the top of the rim. The cell was held at 90° angle and excess material was skimmed off. Weight of the sample with polymer was measured. Similarly measurements for other polymers were also measured. All the measurements of sample were listed in Table 2 (Model Best-Nr: JR FLW; Serial-Nr: FLW 33S)

EXAMPLE 4

Flow Characterization Measurement of Silica Coated Polymers by Using Johanson Flow Rate Indicizer The same process which was described in Example 3 was repeated by replacing the polymer sample with silica coated polymer sample. All the measurements of sample were listed in Table 2.

TABLE 2

| | Flow and Cohesion characteristics of samples | | | |
|---|---|---|---|---|
| | Processing conditions | | Flow Characterization | Brookfield Cohesion |
| Excipient | RPM (Rotations per minute) | Screen size | (Johanson Flow Rate Index(lb/min) | Coefficient (kPa) |
| Plasdone | control | | 221 | 0.221 |
| Plasdone DC | 3000 | 0.5 | 276 | 0.061 |

TABLE 2-continued

Flow and Cohesion characteristics of samples

| Excipient | Processing conditions | | Flow Characterization | Brookfield Cohesion |
|---|---|---|---|---|
| | RPM (Rotations per minute) | Screen size | (Johanson Flow Rate Index(lb/min) | Coefficient (kPa) |
| Crospovidone | control | | 97 | 0.186 |
| CrospovidoneDC | 3000 | 0.3 | 186 | 0.111 |

EXAMPLE 10

Pharmaceutical Tablet Preparation.

A pharmaceutical tablet was prepared using standard Plasdone™, and Plasdone™ DC. The tablet formula was:

TABLE 4

Tablet Composition

| Tablet Composition | | Addition level |
|---|---|---|
| Standard | Invention | (%) |
| Plasdone ® | Plasdone ® DC | 50 |
| Theophyline | | 25 |
| Fastflo ® Lactose | | 24.5 |
| Magnesium stearate | | 0.5 |
| Total | | 100 |

Hardness of the tablet formulations comprising standard Plasdone® and Plasdone® DC was measured and found to be at least 20 N The compatibility of tablets containing the compressed excipient of this invention can be at least 20 N over tablets with comparable quantities of the same incorporated excipients.

The present invention also provides applications of the coprocessed excipient in paints and coatings, personal care, detergents, pharmaceuticals, neutraceuticals, pet food, animal food, agricultural products, adhesives, electroplating, inks, dyes, paper, catalytic convertors, ceramics, insulators, and electronics.

The invention has been described in detail with particular reference to preferred embodiments thereof, but it will be understood that variations and modifications can be effected within the spirit and scope of the invention.

We claim:

1. A coprocessed excipient comprising:
   about 90.0% to about 99.9% of w/w a vinyl lactam derived polymer comprising a monomer selected from the group consisting of N-vinyl-2-pyrrolidone, N-vinyl-2-caprolactam, N-vinyl-3-methyl-2-pyrrolidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5,5-dimethyl-2-pyrrolidone, N-vinyl-3,3,5 -trimethyl-2-pyrrolidone, N-vinyl-5-methyl-5-ethyl-2-pyrrolidone, N-vinyl-3,4,5-trimethyl-3-ethyl-2-pyrrolidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, and combinations thereof; and
   about 0.1% w/w to about 10.0% w/w of a deagglomerated coprocessing agent comprising a silica having a particle size less than 500 nm, where the coprocessing agent is deagglomerated using shear in magnitude of at least 0.01 kW-hour/kilogram;
   wherein the coprocessed excipient is prepared in a continuous process, where the coprocessing results in silica coating of the vinyl lactam derived polymer, and the coprocessed excipient has a Brookfield cohesion of less than 0.12 kPa and a bulk density of at least 0.249 gram/milliliter,
   wherein the silica is selected from the group consisting of a fumed silica, a colloidal silica, a silicon dioxide, a calcium silicate and combinations thereof.

2. The coprocessed excipient of claim 1, wherein the vinyl lactam derived polymer is selected from the group consisting of poly(vinyl pyrrolidone), polyvinyl poly pyrrolidone, and combinations thereof.

3. The coprocessed excipient of claim 1, wherein the lactam derived polymer and the coprocessing agent are present in a ratio from about 90:10 to 99.9 to 0.1.

4. The coprocessed excipient of claim 1, wherein the coprocessed excipient is further combined with an active or functional ingredient selected from the group consisting of a paint, a coating, a personal care ingredient, a detergent, a pharmaceutical, a nutraceutical, a ceramic, an insulator, a pet food animal food, a human food, an agricultural product, an adhesive, an electroplating ingredient, an ink, a dye, a paper ingredient, a catalytic convertor, an electronic, and combinations thereof.

5. A continuous process for preparing a coprocessed excipient according to claim 1 comprising the steps of:
   i. deagglomerating a coprocessing agent comprising a silica using shear in magnitude of at least 0.01 kW-hour/kilogram;
   ii. passing a lactam derived polymer and the deagglomerated coprocessing agent through a blender with an average particle residence time of >1 second;
   iii. subjecting the above two components to pass through a universal mill;
   iv. maintaining an average particle residence time within the universal mill system to be >1 seconds completed by a continuous recycle process; and
   v. obtaining the coprocessed excipient according to claim 1 having a Brookfield cohesion of less than 0.12 kPa and a bulk density of at least 0.249 gram/milliliter, wherein the vinyl lactam derived polymer comprises a monomer selected from the group consisting of N-vinyl-2-pyrrolidone, N-vinyl-2-caprolactam, N-vinyl-3-methyl-2-pyrrolidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5,5-dimethyl-2-pyrrolidone, N-vinyl-3,3,5 -trimethyl-2-pyrrolidone, N-vinyl-5-methyl-5-ethyl-2-pyrrolidone, N-vinyl-3,4,5-trimethyl-3-ethyl-2-pyrrolidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, N-vinyl-3,5,7-trimethyl-2-caprolactam, and combinations thereof.

6. The process of claim 5, wherein the universal mill consists of a rotor with tip speed of about 15 meters/second to about 150 meters/second and screen size of about 0.2 millimeter to about 0.9 millimeter.

7. A composition comprising the coprocessed excipient of claim 1 for use in an industrial application selected from paints and coatings, personal care, detergents, pharmaceuticals, nutraceuticals, ceramics, insulators, pet food, animal food and human food, agricultural products, adhesives, electroplating, inks, dyes, paper, catalytic convertors and electronics.

8. The composition of claim 7, wherein the composition is used in pharmaceuticals.

9. The composition of claim 8, wherein the composition is formulated into an oral dosage form by dry granulation, direct compression, or hot melt extrusion processing.

10. A directly compressible pharmaceutical composition comprising:

i. an active pharmaceutical ingredient;
   ii. the coprocessed excipient of claim 1; and
   iii. optionally one or more pharmaceutically acceptable additives.

11. The directly compressible pharmaceutical composition of claim 10, wherein the composition is formulated into modified release, controlled release, sustained release, extended release dosage forms or immediate release and soluble dosage form.

12. The directly compressible pharmaceutical composition of claim 10, wherein the compactability of the tablet containing coprocessed excipient is at least 20 N over tablets made with the same uncoprocessed excipients.

13. The process of preparing the directly the compressible pharmaceutical composition of claim 10, comprising the steps of:

i. blending the active pharmaceutical ingredient, the coprocessed excipient of claim 1, and optionally one or more adjuvants: and
   ii. compressing the resulting components to obtain directly compressible pharmaceutical composition.

\* \* \* \* \*